(12) United States Patent  (10) Patent No.: US 7,405,297 B2
Furneaux et al.  (45) Date of Patent: Jul. 29, 2008

(54) PROCESS FOR PREPARING INHIBITORS OF NUCLEOSIDE METABOLISM

(75) Inventors: Richard Hubert Furneaux, Wellington (NZ); Peter Charles Tyler, Wellington (NZ); Vern L. Schramm, New Rochelle, NY (US)

(73) Assignees: Industrial Research Limited, Lower Hutt (NZ); Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 11/716,100

(22) Filed: Mar. 9, 2007

(65) Prior Publication Data

US 2007/0161667 A1    Jul. 12, 2007

Related U.S. Application Data

(60) Division of application No. 11/297,954, filed on Dec. 8, 2005, now Pat. No. 7,211,677, which is a division of application No. 10/737,724, filed on Dec. 16, 2003, now Pat. No. 7,022,852, which is a continuation of application No. 09/958,219, filed as application No. PCT/NZ00/00048 on Apr. 7, 2000, now Pat. No. 6,693,193.

(30) Foreign Application Priority Data

Apr. 8, 1999 (NZ) .................................... 335090
Jun. 8, 1999 (NZ) .................................... 336168

(51) Int. Cl.
*C07D 487/04* (2006.01)
*C07D 207/30* (2006.01)

(52) U.S. Cl. .................. 544/280; 544/224; 544/242; 548/530; 548/531; 548/532

(58) Field of Classification Search ................ 544/224, 544/242, 280; 548/530, 531, 532
See application file for complete search history.

(56) References Cited

U.S. PATENT DOCUMENTS 5,985,848 A    11/1999    Furneaux et al.

(Continued)

FOREIGN PATENT DOCUMENTS

WO    WO 94/11534    5/1994

(Continued)

OTHER PUBLICATIONS

Banker G S et al., entitled "Modern Pharmaceutics," Marcel Dekker Inc., Third Edition, Revised and Expanded, 1996, pp. 451 & 596.

(Continued)

*Primary Examiner*—Golam M Shameem
(74) *Attorney, Agent, or Firm*—Amster, Rothstein & Ebenstein LLP

(57) ABSTRACT

A process of preparing a compound of the formula (I)

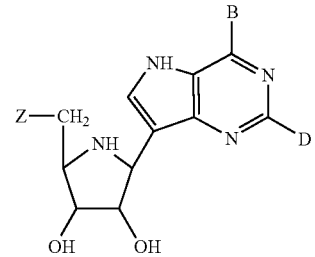

wherein B is chosen from OH, $NH_2$, NHR, H or halogen; D is chosen from OH, $NH_2$, NHR, H halogen or $SCH_3$; R is an optionally substituted alkyl, aralkyl or aryl group; and Z is selected from OH, hydrogen, halogen, hydroxy, SQ or OQ, Q is an optionally substituted alkyl, aralkyl or aryl group; or a tautomer thereof; or a pharmaceutically acceptable salt thereof; or an ester thereof; or a prodrug thereof, which comprises reacting a compound of the formula (II)

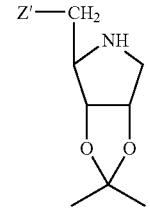

with an anion produced by abstraction of the bromine or iodine atom from a compound of formula (XIX),

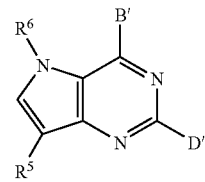

to form a compound of formula (XX)

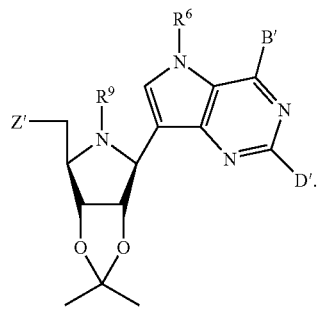

The compound of formula (XX) is N- and O-deprotected to obtain the compound of formula (I).

4 Claims, No Drawings

U.S. PATENT DOCUMENTS

| | | | |
|---|---|---|---|
| 6,066,722 | A | 5/2000 | Furneaux et al. |
| 6,228,847 | B1 | 5/2001 | Furneaux et al. |
| 6,379,911 | B2 | 4/2002 | Schramm et al. |
| 6,458,799 | B1 | 10/2002 | Montgomery et al. |
| 6,492,347 | B2 | 12/2002 | Furneaux et al. |
| 6,583,154 | B1 | 6/2003 | Norman et al. |
| 6,693,193 | B1 | 2/2004 | Furneaux et al. |
| 6,764,829 | B2 | 7/2004 | Schramm et al. |
| 6,803,455 | B2 | 10/2004 | Furneaux et al. |
| 7,022,852 | B2 | 4/2006 | Furneaux et al. |
| 7,098,334 | B2 | 8/2006 | Furneaux et al. |
| 7,109,331 | B2 | 9/2006 | Furneaux et al. |
| 7,211,653 | B2 | 5/2007 | Furneaux et al. |
| 7,211,677 | B2 | 5/2007 | Furneaux et al. |
| 2006/0160765 | A1 | 7/2006 | Evans et al. |
| 2006/0217551 | A1 | 9/2006 | Evans et al. |

FOREIGN PATENT DOCUMENTS

| | | |
|---|---|---|
| WO | WO 99/19338 | 4/1999 |
| WO | WO 2004/018496 A1 | 3/2004 |
| WO | WO 2005/118532 | 12/2005 |
| WO | WO 2006/014913 A2 | 2/2006 |
| WO | WO 2006/123953 A1 | 11/2006 |
| WO | WO 2007/069923 A1 | 6/2007 |
| WO | WO 2007/097647 A1 | 8/2007 |
| WO | WO 2007/097648 A1 | 8/2007 |

OTHER PUBLICATIONS

"Biocryst Pharmaceuticals, Inc. Announces Preliminary Phase II Trial Data for a Topical Ointment formulation of PNP Drug Drug Candidate, BCX-34," Biocryst News, Apr. 29, 1998.

Evans G B et al., entitled "Exploring structure-activity relationships of transition state analogues of human purine nucleoside phosphorylase," J. Med. Chem. 2003, 46, 3412-3423.

Evans G B et al. "Synthesis of a transition state analogue inhibitor of purine nucleoside phosphorylase via the Mannich reaction," Organic Letters 2003, 5(20), 3639-3640.

Filichev V V et al., entitled "Synthesis of 1'-aza-C-nucleosides from (3R,4R)-4-(hydroxymethyl)pyrrolidin-3-ol," Tetrahedron 57 (2001) 9163-9168.

Galeazzi, R et al., "Chiral 3-hydroxypyrrolidin-2-ones from a Baylis-Hillman adduct: convergent, stereoselective synthesis of a glycosidase inhibitor," Tertrahedron: Asymmetry, 2004 vol. 15 pp. 3249-3256.

Kamath V P et al., entitled "Synthesis of a potent transition-state inhibitor of 5'-Deoxy-5'-methylthioadenosine phosphorylase," J. Med. Chem. 2004, 47, 1322-1324.

Kametani, T et al., "Studies on the Syntheses of Heterocyclic Compounds. 762. Synthesis of 3-benzyl-6-methyl-2-oxo-3,6-diazabicyclo[3.1.0]hexane as a synthetic intermediate of mitomycins," Tetrahedron, 1979, 35(3), pp. 313-316.

Karlsson S et al., entitled "Synthesis of enantiomerically pure 4-substituted pyrrolidin-3-ols via asymmetric 1,3-dipolar cycloaddition," Tetrahedron: Asymmetry 12 (2001) 1977-1982.

Lewandowicz A et al., entitled "Over-the barrier transition state analoques and crystal structure with *Mycobacterium tubersulosis* purine nucleoside phosphorylase," Biochemistry 2003, 42, 6057-6066.

Lewandowicz A et al. "Energetic Mapping of Transition State Analogue Internations with Human and *Plasmodium falciparum* Purine Nucleotide Phosphorylases" Journal of Biological Chemistry, 2005, 280(34), 30320-30328.

STN File CA Abstract No. 91-123648 (2005.

Wolff M E, entitled "Burger's Medicinal Chemistry and Drug Discovery," Fifth Edition, vol. 1: Principles and Practice, John Wiley & Sons, 1995, 975-977.

Braunheim, B.B. et al., "Prediction of Inhibitor Binding Free Energies by Quantum Neural Networks. Nucleoside Analogues Binding to Trypanosomal Nucleoside Hydrolase". Biochemistry, Nov. 12, 1999, vol. 38, No. 49, 16076-16083.

Miiles, R.W. et al., "Iminoribitol Transition State Analogue Inhibitors of Protozoan Nucleoside Hydrolases". Biochemistry, Sep. 11, 1999, vol. 38, No. 40, 13147-13154.

Shi, W. et al., "The 2.0 Ang Structure of Malarial Purine Phosphoribosyltransferase in Complex with a Transition State Analogue Inhibitor". Biochemistry, Jul. 13, 1999, vol. 38, No. 31, 9872-9880.

Li, C. et al., "Transition-State Analogs as Inhibitors of Human and Malarial Hypoxanthine-guanine Phosphoribosyltransferases". Nat. Struct. Biol., 1999, vol. 6, No. 6, 582-587.

Miles, R. W. et al., "Purine Nucleoside Phosphorylase. Transition State Structure, Transition State Inhibitors and One-Third-The-Sites Reactivity". Biomed. Health Res. Series, vol. 27 (Enzymatic Mechanisms, Frey & Northrop, eds), 32-47, 1999. IOS Press.

Furneaux, R.H. et al., "Improved Synthesis of 3H,5H-Pyrrolo[3,2,-d] pyrimidines". J. Org. Chem, 1999, vol. 64, No. 22, 8411-8412.

Miles, R.W. et al., "One-Third-The-Sites Transition-State Inhibitors for Purine Nucleoside Phosphorolase". Biochemistry, 1998, vol. 37, No. 24, 8615-8621.

Elliot, A. J. et al., "A Short, Facile Sythesis of 2-aminio-1,5-dihydro-4H-pyrrolo[3,2-d]-pyrimidin-4-one (9-deazaguanine)". Tetrahedron Lett., 1996, vol. 37, No. 25, 4339-43.

Brakta, M. et al., "Efficient Synthesis of 3H,5H-pyrrolo[3,2-d]pyrimidin-4-one". J, Chem. Soc., Perkin Trans. 1, 1992, vol. 15, 1883-1884.

Taylor, E. C. et al., entitled "An Expeditious Synthesis of 2-Amino-4(3H)-oxo-5H-pyrrolo [3, 2-d] pyrimidine (9-Deazaguanine)" Tetrahedron Letters, vol. 34, No. 29, 1993, pp. 4595-4598.

Lim M-I et al., entitled "A New Synthesis of Pyrrolo[3, 2-d]pyrimidines ("9-Deazapurines") via 3-Amino-2-carboalkoxypyrroles" Journal of Organic Chemistry, vol. 44, No. 22, Oct. 26, 1979, pp. 3826-3829.

Lim, Mu-III et al., entitled "Synthesis of "9-deazaguanosine" and other new pyrrolo [3, 2-d] pyrimidine C-nucleosides" J. Org. Chem. (1983), 48(6), 780-8.

Elliott, Arthur J. et al., entitled "An Improved Synthesis of 7-substituted Pyrrolo [3, 2-d]pyrimidines" Journal of Organic Chemistry (1997), 62(23), 8071-8075.

Ciller, Juan A. et al., "Ring Transformation of Isoxazoles into Furan and Pyran Derivatives" J. Chem. Soc. Perkin Trans. I, 1985, pp. 2581-2584.

Furneaux, R. H. et al., entitled "Synthesis of Transition State Inhibitors for N-Riboside Hydrolases and Transferases," Tetrahedron, vol. 53, No. 8, pp. 2915-2930, 1997.

PROCESS FOR PREPARING INHIBITORS OF NUCLEOSIDE METABOLISM

CROSS-REFERENCE TO RELATED APPLICATIONS

This application is a divisional of U.S. patent application Ser. No. 11/297,954, filed Dec. 8, 2005, now U.S. Pat. No. 7,211,677, which is a divisional of U.S. patent application Ser. No. 10/737,724, filed Dec. 16, 2003, now U.S. Pat. No. 7,022,852, issued Apr. 4, 2006, which is a continuation of U.S. patent application Ser. No. 09/958,219, filed Apr. 18, 2002, now U.S. Pat. No. 6,693,193 B1, issued Feb. 17, 2004, which is a U.S. National Phase Filing under 35 U.S.C. §371 of PCT International Application No. PCT/NZ00/00048, filed on Apr. 7, 2000, and claims priority to New Zealand Patent Application No. NZ 336168, filed on Jun. 8, 1999 and New Zealand Patent Application No. NZ 335090, filed on Apr. 8, 1999, the contents of all of which are hereby incorporated by reference in their entirety.

STATEMENT OF GOVERNMENT SUPPORT

The invention disclosed herein was made with U.S. Government support under grant number GM41916 from the National Institutes of Health, U.S. Department of Health and Human Services. Accordingly, the U.S. Government has certain rights in this invention.

TECHNICAL FIELD

This invention relates to processes for the preparation of certain nucleoside analogues, to new intermediate compounds useful in such processes, and to the preparation of intermediate compounds useful in such processes.

BACKGROUND ART

Compounds which are potent inhibitors of purine nucleoside phosphorylase and are useful for suppressing T-cell function and/or treating and/or preventing infections caused by protozoan parasites are described in *Biochemistry*, 1998, 37, 8615-8621 and in our co-pending PCT International Patent Application No. PCT/US98/21717 (WO 99/19338).

There remains a need for alternate, simpler methods of preparing these compounds.

It is therefore an object of the present invention to provide an alternate process for preparing these compounds, which will at least provide the public with a useful choice.

SUMMARY OF THE MENTION

In a first aspect, the present invention provides a process of preparing a compound of the formula

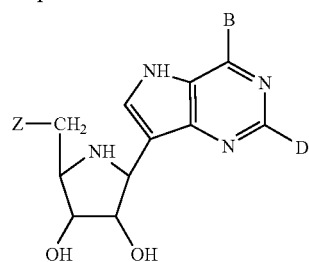

(I)

wherein B is chosen from OH, $NH_2$, NHR, H or halogen; D is chosen from OH, $NH_2$, NHR, H, halogen or $SCH_3$; R is an optionally substituted alkyl, aralkyl or aryl group; and Z is selected from OH, hydrogen, halogen, hydroxy, SQ or OQ, Q is an optionally substituted alkyl, aralkyl or aryl group; or a tautomer thereof; or a pharmaceutically acceptable salt thereof; or an ester thereof; or a prodrug thereof, wherein the process comprises the following steps:

(a) reacting a compound of the formula (II)

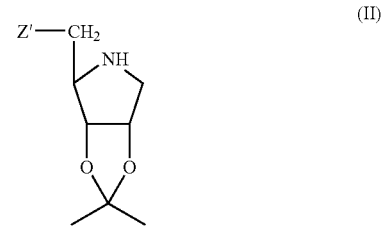

(II)

wherein Z' is a hydrogen or halogen atom, a group of formula SQ or OQ, or a trialkylsilyloxy, alkyldiarylsilyloxy or optionally substituted triarylmethoxy group and Q is an optionally substituted alkyl, aralkyl or aryl group, sequentially with a halogenating agent and a sterically hindered base to form an imine;

(b) condensing the imine thus prepared with an anion produced by abstraction of the bromine or iodine atom from a compound of formula (XIX):

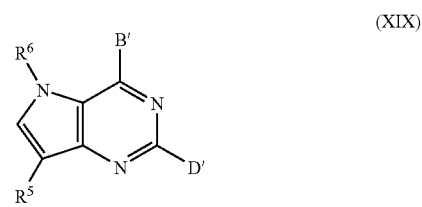

(XIX)

wherein $R^5$ is a bromine or iodine atom, $R^6$ is an N-protecting group, B' and D' are independently selected from H, $OR^7$ and $N(R^8)_2$, and $R^7$ and $R^8$ are O- and N-protecting groups respectively, to produce a 1-C-(pyrrolo[3,2-d]pyrimidin-7-yl)-1,4-dideoxy-1,4-imino-2,3-O-isopropylidene-D-ribitol derivative of formula (XX):

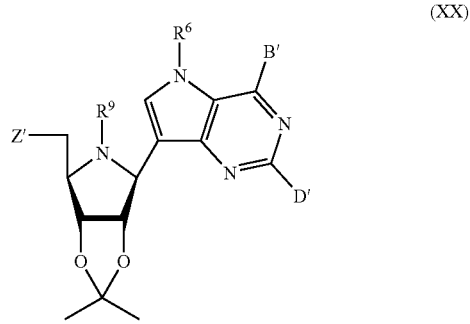

(XX)

wherein $R^9$ is a hydrogen atom, Z' is as defined above for compounds of formula (II) and $R^6$, B' and D' are as defined above for compounds of formula (XIX);

(c) optionally, converting the compound of formula (XX) to a compound of formula (XX) wherein Z', $R^6$, B' and D' are as defined above but $R^9$ is alkoxycarbonyl or aralkoxycarbonyl, or optionally, where Z' in the compound of formula (XX) is trialkylsilyloxy, alkyldiarylsilyloxy or optionally substituted triarylmethoxy, converting the compound of formula (XX) to a compound of formula (XX) wherein $R^6$, $R^9$, B' and D' are as defined above but Z' is OH; and (d) N- and O-deprotecting the compound of formula (XX) prepared from step (b) or (c), by acid- or alkali-catalyzed hydrolysis or alcoholysis or catalytic hydrogenolysis as required for the O- and N-protecting groups in use, to produce a compound of the formula (I) as defined above.

Where a pharmaceutically acceptable salt, ester or prodrug of the compound of formula (I) is desired, the process will also include the further step of converting the compound of formula (I) thus prepared to the desired pharmaceutically acceptable salt, ester or prodrug, using methods known in the art.

In a preferred embodiment, the halogenating agent used in step (a) is N-chlorosuccinimide.

In a preferred embodiment, the hindered base used in step (a) is lithium tetramethyl piperidide.

Preferably, in step (b) the bromine or iodine atom is abstracted from the compound of formula (XIX) using butyllithium or magnesium.

Preferably, the N-protecting group $R^6$ in the compound of formula (XIX) is an alkoxymethyl group (such as benzyloxymethyl), a silyl group (such as tert-butyldimethylsilyl) or an arylmethyl group (such as benzyl).

Preferably, the O-protecting group $R^7$ is an alkyl or arylmethyl group (such as methyl, tert-butyl or benzyl).

Preferably, each N-protecting group $R^8$ is independently an arylmethyl group (such as benzyl or 4-methoxybenzyl), or the two $R^8$ groups together form the 2,4-hexadien-2,5-yl group.

In a further aspect, the present invention provides a compound of formula (XX):

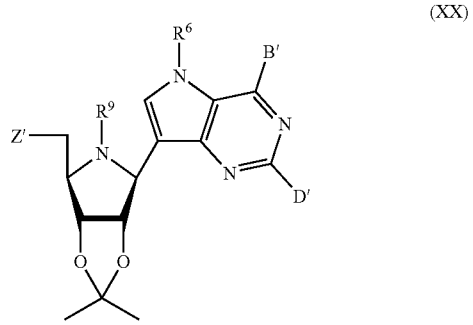

(XX)

wherein $R^9$ is a hydrogen atom, an alkoxycarbonyl or aralkyloxycarbonyl group, Z' is a hydrogen or halogen atom, a hydroxy group, a group of formula SQ or OQ, or a trialkylsilyloxy, alkyldiarylsilyloxy or optionally substituted triarylmethoxy group and Q is an optionally substituted alkyl, aralkyl or aryl group, and $R^6$ is an N-protecting group, B' and D' are independently selected from H, $OR^7$ and $N(R^8)_2$, and $R^7$ and $R^8$ are O- and N-protecting groups respectively.

Preferred are compounds of formula (XX) wherein $R^9$ is a hydrogen atom or a tert-butoxycarbonyl group, Z' is a hydroxy group, a tert-butyldimethylsilyloxy or methylthio group, and $R^6$ is a benzyloxymethyl, allyl, tert-butyldimethylsilyl, 2-(trimethylsilylethoxy)methyl or benzyl group, B' is a methoxy, tert-butoxy or benzyloxy group and D' is a hydrogen or fluorine atom, a dibenzylamino group or a bis(4-methoxybenzyl)amino group.

In a further aspect, the present invention provides a process of preparing a compound of formula (XX) as defined above, wherein the process comprises the steps (a) and (b) as defined above for preparing compounds of the formula (I); and optionally (a) converting $R^9$ from a hydrogen atom to an alkoxycarbonyl or aralkyloxycarbonyl group by reaction with an alkoxycarbonylating or aralkyloxycarbonylating reagent; or (b) converting Z' from a trialkylsilyloxy, alkyldiarylsilyloxy or optionally substituted triarylmethoxy group to a hydroxy group by reaction with a source of fluoride or acid.

In a further aspect, the present invention provides a process of preparing a compound of the formula (I) as defined above, or a pharmaceutically acceptable salt, ester or prodrug thereof, comprising the step of N- and O-deprotecting a compound of the formula (XX) as defined above by acid- or alkali-catalyzed hydrolysis or alcoholysis or catalytic hydrogenolysis, as required for the O- and N-protecting groups in use, to produce a compound of the formula (I) as defined above.

In further aspects, the present invention provides compounds of the formula (I) and (XX) when prepared by processes as defined above.

In a further aspect, the present invention provides a process of preparing the compound 2-amino-3H,5H-pyrrolo[3,2-d]pyrimidin-4-one, comprising the step of reacting the compound 2-(N-dimethylaminomethylene)amino-6-(2-dimethylaminovinyl)-5-nitropyrimid-4-one with a reagent capable of reducing the nitro group, to produce the compound 2-amino-3H,5H-pyrrolo[3,2-d]pyrimidin-4-one.

Preferably, the reducing agent used is aqueous sodium dithionite. Alternatively, the reduction may be carried out using catalytic hydrogenation. Where the reagent is aqueous sodium dithionite (a preferred reagent), the process is preferably carried out at elevated temperature, preferably at about 100° C.

Preferably, the process includes the initial step of preparing the compound 2-(N-dimethylaminomethylene)amino-6-(2-dimethylaminovinyl)-nitropyrimidin-4-one by reacting the compound 2-amino-6-methyl-5-nitro-pyrimidin-4-one with a reagent capable of effecting dialkylaminomethylation.

Preferably, the reagent used to effect the dialkylaminomethylation is a combination of DMF dimethylacetal and DMF.

Preferably, this step is carried out with heating at about 100° C.

Alternatively, the reagent may be Bredereck's reagent (t-butoxy bis(dimethylamino)methane).

In a further aspect, the invention provides the compound 2-amino-3H,5H-pyrrolo[3,2-d]pyrimidin-4-one when prepared by a process as defined above.

In a further aspect, the invention provides a compound of the formula:

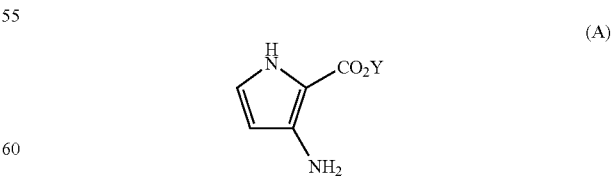

(A)

wherein Y is an unsubstituted or substituted alkyl or arylalkyl group having 1 to 8 carbon atoms.

In another aspect, the invention provides a process of preparing the compound 3H,5H-pyrrolo[3,2-d]pyrimidin-4-one, comprising the step of reacting a compound of the formula (A) defined above with a reagent capable of delivering a formyl equivalent.

Preferably, the reagent used is formamidine acetate.

Preferably, the compound of formula (A) is the compound 3-amino-2-ethoxycarbonylpyrrole.

Conveniently, the reaction is carried out in refluxing ethanol.

In still a further aspect, the invention provides a process of preparing a compound of the formula (A) defined above, comprising the following steps:
(a) reacting isoxazole with alkoxide ions in the presence of an alcohol;
(b) quenching the reaction with an acid;
(c) reacting the resulting reaction mixture with a dialkyl aminomalonate;
(d) isolating an organic phase of the resulting reaction mixture and reducing it to a residue; and
(e) reacting the residue from the organic phase with a base in a protic or aprotic solvent to produce a compound of formula (A).

Preferably, step (e) comprises reacting the residue from the organic phase with alkoxide ions in excess alcohol.

In a preferred embodiment, the compound of formula A is 3-amino-2-ethoxycarbonylpyrrole. In this embodiment, the alcohol used in excess in step (e) is ethanol and the alkoxide ions are ethoxide ions.

In still a further aspect, the present invention provides a process of preparing the compound 3H,5H-pyrrolo[3,2-d]pyrimidin-4-one, comprising the following steps:
(a) preparing a compound of formula (A) by a process as defined above; and
(b) reacting the compound of formula (A) thus prepared with a reagent capable of delivering a formyl equivalent.

In another aspect, the invention provides the compound 3H,5H-pyrrolo[3,2-d]pyrimidin-4-one when prepared by a process as defined above.

In yet a further aspect, the present invention provides a process for preparing the compound of formula 3 or 4 (defined below), respectively:

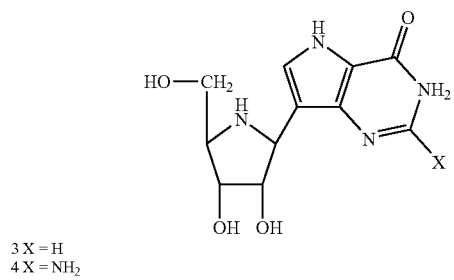

3 X = H
4 X = NH$_2$ comprising the steps of:
(1) carrying out N,O-protection of the compound 3H,5H-pyrrolo[3,2-d]pyrimidin-4-one or 2-amino-3H,5H-pyrrolo[3,2-d]pyrimidin-4-one, respectively;
(2) brominating the protected compound at C7;
(3) lithiation of the resulting brominated compound;
(4) addition of the resulting lithiated species to a protected imine, specifically a 2,3,5-tri-O-protected 1,N-dehydro-1,4-dideoxy-1,4-imino-D-ribitol; and
(5) carrying out N,O-deprotection of the resulting species to produce the compound 3 or 4, respectively, as defined above.

In still a further aspect, the present invention provides a method of preparing the compound 3 or 4, respectively, as defined above, comprising the following steps:
(a) preparing the compound 3H,5H-pyrrolo[3,2-d]pyrimidin-4-one or 4-amino-3H,5H-pyrrolo[3,2-d]pyrimidin-4-one, respectively, by a method as defined above;
(b) carrying out N,O-protection of the compound 3H,5H-pyrrolo[3,2-d]pyrimidin-4-one or 2-amino-3H,5H-pyrrolo[3,2-d]pyrimidin-4-one, respectively;
(c) brominating, the protected compound at C7;
(d) lithiation of the resulting brominated compound;
(e) addition of the resulting lithiated species to a protected imine, specifically a 2,3,5-tri-O-protected 1,N-dehydro-1,4-dideoxy-1,4-imino-D-ribitol; and
(f) carrying out N,O-deprotection of the resulting species to produce the compound 3 or 4, respectively, as defined above.

Although the present invention is broadly as defined above, it is not limited thereto and also includes embodiments of which the following description provides examples.

DETAILED DESCRIPTION OF THE INVENTION

As defined above, the present invention provides a new process of preparing the compounds of formula (I) as defined above, or tautomers, pharmaceutically acceptable salts, esters or prodrugs thereof. These compounds and various methods for preparing them are described in International Patent Publication No. WO 99/19338, the contents of which are incorporated by reference.

The process of the present invention represents an alternate method of preparing the compounds of formula (I). The process of the present invention is a convergent synthesis route rather than a linear one. This means that it has the advantage of being able to provide higher yields of the compounds of formula (I) as well as providing a more practical route to these compounds than those previously described.

The process of the present invention comprises the step of reacting a compound of the formula (II) (as defined above) sequentially with a halogenating agent, such as N-chlorosuccinimide, and a sterically hindered base, to form an imine. The imine thus prepared is then condensed with an anion produced by abstraction of the bromine or iodine atom from a compound of the formula (XIX) as defined above, to form a compound of formula (XX) as defined above. This is followed by N- and O-deprotection of a compound of formula (XX) to produce a compound of formula (I). If desired, the compound of formula (I) thus prepared may be converted into a pharmaceutically acceptable salt, ester or prodrug thereof, using methods known in the art.

Particularly suitable as N-protecting, groups $R^6$ in the compound of formula (XIX) are alkoxymethyl groups such as benzyloxymethyl, silyl groups such as tert-butyldimethylsilyl, and arylmethyl groups such as benzyl.

Particularly suitable as O-protecting groups $R^7$ in the compound of formula (XIX) are alkyl or arylmethyl groups such as methyl, tert-butyl or benzyl.

Particularly suitable as N-protecting groups $R^8$ in the compound of formula (XIX) are arylmethyl groups such as benzyl or 4-methoxybenzyl, or the two $R^8$ groups may together form the 2,4-hexadien-2,5-yl group.

Examples of preferred values for the groups R and Q in the compounds of formulae (I) and (II) are methyl, ethyl and benzyl. Suitable substituents for the groups R and Q include halogen, preferably fluorine.

The compounds of formula (XIX) defined above may be prepared by conventional methods such as those detailed herein.

In particular, unprotected deazapurines can be converted by conventional methods into their protected forms (XIX).

Thus, 9-deazahypoxanthine can be treated with a chlorinating reagent, preferably phosphoryl chloride, to form the 6-chloro-9-deazapurine. After N-protection, the chlorine is displaced with alkoxide ion. The resulting N,O-protected deazapurine is then 9-halogenated.

Alternatively, known 5-nitro-6-methylpyrimidine derivatives can first be converted into suitably protected intermediates, and then cyclized to the corresponding deazapurines, for example by reaction with tert-butoxy-bis(dimethylamino) methane, and then N-protected.

Thus, 5-nitro-6-methyl-pyrimidin-2,4-dione can be sequentially (i) chlorinated, preferably with a reagent such as phosphoryl chloride; (ii) reacted with alkoxide to displace chloride; (iii) treated with a reagent capable of delivering a formyl equivalent, especially a dimethylaminomethylating agent, preferably Bredereck's reagent; (iv) treated with a reducing agent to reduce the nitro group and cause cyclization; and in either order (v) N-protected and (vi) halogenated.

Further, 5-nitro-6-methyl-2-acetamido-pyrimidin-4-one can be sequentially (i) chlorinated, preferably with a reagent such as phosphoryl chloride; (ii) reacted with alkoxide to displace chloride and effect N-deacetylation; (iii) treated with a reagent capable of delivering a formyl equivalent, especially a dimethylaminomethylating agent, preferably Bredereck's reagent; (iv) treated with a reducing agent to reduce the nitro group and cause cyclization; (v) N-protected on the pyrrole nitrogen; (vi) saponified to remove an N-formyl group; and in either order (vi) N-protected and (viii) halogenated.

Compounds of the formula (II) defined above may also be prepared by known methods, as described in WO 99/19338 and the references cited therein.

Suitable reagents for halogenation of a compound of formula (II) include chlorinating or brominating agents, and these include N-chloro- and bromoamides, chlorine and bromine, preferably N-chlorosuccinimide. Halogenation is conveniently carried out at ambient temperatures in an alkane as solvent, preferably hexane, more preferably pentane. Where the halogenation reagent is N-chlorosuccinimide, the succinimide byproduct and any excess reagent can be removed by filtration. An excess of the halogenation reagent can be employed, though it is preferable to use close to equimolar quantity.

Suitable sterically hindered bases that can be used to form the imine by dehalogenation include alkali metal salts of bulky alcohols or amines, such as potassium tert-butoxide, lithium diisopropylamide or preferably lithium tetramethylpiperadide. An excess of base can be employed, though it is preferable to use close to an equimolar quantity. Preferably the amount of base used is determined experimentally as just sufficient to result in complete reaction of the compound of formula (XIX), and this can be judged by thin layer chromatography.

The imine formed by halogenation and dehydrohalogenation of a compound of formula (II) is more stable when kept at room temperature or below, but does not readily condense with the anion produced by abstraction of bromine or iodine from a compound of formula (XIX) at temperatures below −40° C. The anion can be prepared at temperatures of −35 to −75° C., but the temperature of the reaction medium should be in the range of −20 to +10° C. to effect the condensation reaction. The anion is unstable at temperatures above +10° C., and is preferably kept at temperatures below 0° C., more preferably at or below −10° C. The anion can be more stable in diethyl ether solution, and this is the preferred solvent. Compounds of formula (XIX) and the anions formed from them can have limited solubility in diethyl ether, however, so that addition of a further solvent to assist with solubility is sometimes necessary. In this case the favoured solvent is anisole, so that the favoured reaction medium is a mixture of diethyl ether and anisole, the proportions being chosen to optimize solubility and stability of the reactants. An excess of either the anion or the imine can be employed, though it is preferable to use close to equimolar quantities of these reactants. As a small portion of the anion can be quenched by proton abstraction reactions or be subject to degradation reactions at the temperatures required to effect coupling, it is sometimes preferable to use a small excess of the anion, up to 2 equivalents, preferably up to 1.2 equivalents.

Examples of preferred reagents for performing the abstraction of the bromine or iodine atom from the compound of formula (XIX) are butyllithium or magnesium, although other suitable reagents will be apparent to those skilled in the art.

The above condensation reaction produces a compound of the formula (XX) as defined above.

In some instances, in order to facilitate purification, a derivative of formula (XX) wherein Z' is a trialkylsilyloxy, alkyldiarylsilyloxy or optionally substituted triarylmethoxy group (such as trityloxy (ie unsubstituted triphenylmethoxy) or 4-monomethoxy or 4,4'-dimethoxytrityloxy) and $R^9$ is a hydrogen atom can be further converted into a derivative of formula (XX) wherein Z' is a hydroxy group and $R^9$ is a hydrogen atom. For example, in the case wherein Z' is a trialkylsilyloxy or alkyldiarylsilyloxy group, preferably a tert-butyldimethylsilyloxy group, this can be achieved by treatment with tetrabutylammonium fluoride in tetrahydrofuran followed by chromatography.

In some instances, in order to facilitate purification, a derivative of formula (XX) wherein $R^9$ is a hydrogen atom can be further converted into a derivative of formula (XX) wherein $R^9$ is an alkoxycarbonyl or aralkyloxycarbonyl group, preferably a tert-butoxycarbonyl group, for example by treatment with di-tert-butyl dicarbonate in methylene chloride followed by chromatography.

The compound of formula (XIX) (either prepared directly from the condensation reaction or from subsequent conversion to another compound of formula (XX) as described immediately above) is then N- and O-deprotected by acid- or alkali-catalyzed hydrolysis or alcoholysis or catalytic hydrogenolysis as required for the O- and N-protecting groups in use, to produce a compound of the formula (I) as defined above.

Where $R^6$ is a trialkylsilyl (preferably a tert-butyldimethylsilyl), alkyldiarylsilyl or 2-trimethylsilylethoxymethyl group, this group can be removed with a source of fluoride, such as tetrabutylammonium fluoride or hydrogen fluoride pyridine complex, in a solvent such as tetrahydrofuran.

Where B' is a benzyloxy group, and/or $R^6$ is a benzyloxymethyl group, and/or $R^8$ is a benzyl or p-methoxybenzyl group, and/or $R^9$ is an aralkyloxycarbonyl (preferably a benzyloxycarbonyl) group, deprotection can be effected by hydrogenolysis over a metal catalyst. A suitable catalyst is palladium on charcoal, and suitable solvents are ethyl acetate, ethanol and methanol.

Where $R^6$ is a benzyloxymethyl group it can be removed by treatment with a strong acid, such as concentrated hydrochloric acid, the excess acid being removed by evaporation, suitably under reduced pressure. Alternatively it can be removed by hydrogenolysis over a metal catalyst. A suitable catalyst is palladium on charcoal, and suitable solvents are ethyl acetate, ethanol and methanol. Intermediates in these process are compounds wherein $R^6$ is a hydroxymethyl group. This group can resist further reaction under the above conditions but can readily be removed by alkali treatment. Suitable alkaline conditions are ammonia or an alkylamine (such as triethylamine) in water or alcohol solution at room temperature or up to 100° C. The aforementioned hydrogenolysis can be conducted under alkaline conditions to effect full deprotection.

Where B' is a methoxy, tert-butoxy or benzyloxy group, and/or Z' is a trialkylsilyloxy (preferably a tert-butyldimethylsilyloxy) or alkyldiarylsilyloxy group, and/or $R^6$ is a trialkylsilyl (preferably a tert-butyldimethylsilyl), alkyldiarylsilyl, 2-trimethylsilylethoxymethyl or benzyloxymethyl group, and/or $R^9$ is an alkoxycarbonyl or aralkyloxycarbonyl group, especially a tert-butoxycarbonyl group, deprotection can be effected by treatment with aqueous, alcoholic or concentrated acid. Suitable acids are hydrochloric or trifluoroacetic acids. The reaction can be conducted in the range 20-120° C., preferably in concentrated aqueous hydrochloric acid under reflux.

The intermediate compounds of the formula (XX) are novel and constitute a further aspect of the invention.

The compounds of formula (XX) may be prepared by the methods described above. The particular reaction conditions suitable for the production of compounds of formula (XX) will depend upon the particular derivative concerned.

Examples of compounds of the formula (XX) of the invention include the following. The numbering of the table corresponds to the numbering in the Examples which will follow.

tol (compound 3). In this process the compound of formula (II) is 5-O-tert-butyldimethylsilyl-1,4-dideoxy-1,4-imino-2,3-O-isopropylidine-D-ribitol, which is reacted with N-chlorosuccinimide and lithium tetramethylpiperidide to form an imine. The imine is condensed with the anion prepared by abstraction of the bromine atom from the compound 5-N-benzyloxymethyl-7-bromo-4-methoxypyrrolo[3,2-d]pyrimidine using butyllithium. The resulting protected product is then subjected to acid catalysed hydrolysis to perform the deprotection and produce the compound (1S)-1,4-dideoxy-1-C-(4-hydroxypyrrolo[3,2-d]pyrimidin-7-yl)-1,4-imino-D-ribitol.

In the above process, the compound 5-N-benzyloxymethyl-7-bromo-4-methoxypyrrolo[3,2-d]pyrimidine may be prepared by carrying out N,O-protection of the compound 3H,5H-pyrrolo[3,2-d]pyrimidin-4-one and brominating the protected compound at C7.

In further aspects, the present invention provides new processes for preparing other intermediate compounds (besides those of formula (XX)), useful in the process defined above of preparing compounds of formula (I). It also provides certain novel intermediate compounds useful in this process. These aspects of the present invention will now be described in more detail.

In particular, the present invention in certain aspects relates to new processes for preparation of the compounds 3H,5H-pyrrolo[3,2-d]pyrimidin-4-one and 2-amino-3H,5H-pyrrolo[3,2-d]pyrimidin-4-one (1 and 2 shown below).

| Example | $R^b$ | B' | D' | $R^9$ | Z' |
|---------|-------|-----|----|----|----|
| 3.3 | $CH_2OBn$ | OMe | H | H | H |
| 15a | $CH_2OCH_2CH_2SiMe_3$ | OMe | H | H | $SiBu^tMe_2$ |
| 15b | $CH_2CH\!=\!CH_2$ | OMe | H | H | H |
| 15c | $SiBu^tMe_2$ | OBn | F | H | $SiBu^tMe_2$ |
| 15d | $CH_2OBn$ | OBn | F | H | $SiBu^tMe_2$ |
| 15e | $CH_2OCH_2CH_2SiMe_3$ | OBn | H | H | $SiBu^tMe_2$ |
| 15f | $CH_2OBn$ | OBn | H | H | $SiBu^tMe_2$ |
| 15g | $CH_2OBn$ | $OBu^t$ | H | H | $SiBu^tMe_2$ |
| 15h | Bn | OBn | $NBn_2$ | H | $SiBu^tMe_2$ |
| 15i | $CH_2OBn$ | OBn | $N(CH_2C_6H_4\text{-}p\text{-}OMe)_2$ | $CO_2Bu^t$ | $SiBu^tMe_2$ |

One example of the process of the present invention is a process of preparing the compound (1S)-1,4-dideoxy-1-C-(2,4-dihydroxypyrrolo[3,2-d]pyrimidin-7-yl)-1,4-imino-D-ribitol. In this method the compound of formula (II) is 5-O-tert-butyl-dimethylsilyl-1,4-dideoxy-1,4-imino-2,3-O-isopropylidene-D-ribitol, which is reacted with N-chlorosuccinimide and lithium tetramethylpiperidide to form an imine. The imine is condensed with the anion prepared by abstraction of the bromine atom from the compound 7-bromo-5-N-tert-butyldimethylsilyl-2,4-dibenzyloxypyrrolo[3,2-d]pyrimidine using butyl-lithium. The resulting protected product is then subjected to hydrogenolysis in ethanol over palladium in charcoal followed by acid-catalysed alcoholysis in methanol to perform the N- and O-deprotection and produce the compound (1S)-1,4-dideoxy-1-C-(2,4-dihydroxypyrrolo[3,2-d]pyrimidin-7-yl)-1,4-imino-D-ribitol as a salt.

Another example of the process of the present invention is a process of preparing the compound (1S)-1,4-dideoxy-1-C-(4-hydroxypyrrolo[3,2-d]pyrimidin-7-yl)-1,4-imino-D-ribi-

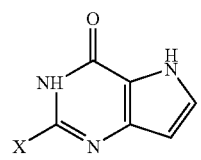

1 X = H
2 X = NH₂

These two compounds are important 9-deaza-isosteres of hypoxanthine and guanine. They are also known inhibitors of purine nucleoside processing enzymes. We have also found that these compounds are useful intermediates which can be used to prepare compounds of the formula (XIX) as defined above, which in turn can be used to prepare the compounds 3 and 4 defined above, respectively, using the convergent synthetic process of the invention for preparing compounds of the formula (I) as defined above. The compounds 3 and 4 are compounds of the general formula (I) which are extremely potent inhibitors of purine nucleoside phosphorylase.

There are relatively few routes to the pyrrolo[3,2-d]pyrimidine ring system.[2] Most start from pyrimidines with appropriate functional groups at the 5 and 6 positions. The first syntheses of 1 and 2 were lengthy and proceeded in poor overall yield.[3] Other syntheses of 1 and 2 have since been reported[4,7] but none is were as simple as we desired.

We have invented new facile syntheses of 1 and 2 that allow ready access to these compounds on a multi-gram scale.

A previous synthesis[6] of 2 (shown in Reaction Scheme 1) started from 2-amino-6-methyl-5-nitropyrimidin-4-one 5 (readily available[8] by nitration of the commercially available 2-amino-6-methylpyrimidin-4-one) which was protected as 6. Chromatography was required at this point to separate the N- and O-pivaloyloxymethyl isomers. Formylation of the 6-methyl group was then accomplished and reduction of 7 with sodium dithionite afforded the pyrrolo[3,2-d]pyrimidine ring system in 8 which was deprotected to give 2. Attempts to formylate the 6-methyl group of 5 directly led only to the N-methyl derivative 9. We have reinvestigated this reaction and now report conditions under which 5 is directly converted into 10 without any apparent formation of the N-methyl compound 9. In particular, 5 may be converted to 10 by reaction with a reagent capable of effecting dialkylaminomethylation. It is preferred that the reagent used is DMF and DMF dimethylacetal. However, those persons skilled in the art will appreciate that alternative reagents, such as Bredereck's reagent, may be used. Reduction of this compound 10 by boiling in aqueous sodium dithionite solution then afforded 2 directly in good yield without recourse to chromatography. Formation of the N-methyl compound is apparently dependent on the concentration of N,N-dimethylformamide used. Lesser amounts will lead to some 9.

It will also be appreciated that the reduction of compound 10 to afford 2 may be effected using any suitable reagent capable of reducing the nitro group on 10. Although a preferred reagent is aqueous sodium dithionite solution, other means of effecting the reduction, such as by catalytic hydrogenation, are within the scope of the invention.

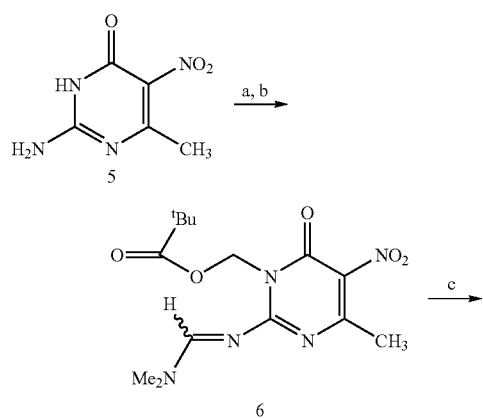

Reaction Scheme 1

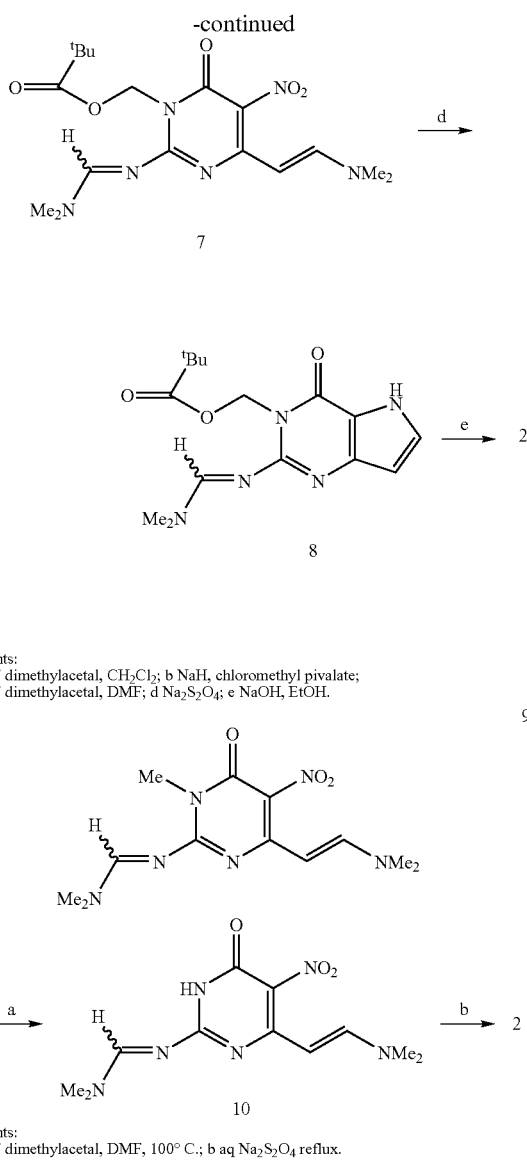

Reagents:
a DMF dimethylacetal, CH$_2$Cl$_2$; b NaH, chloromethyl pivalate; c DMF dimethylacetal, DMF; d Na$_2$S$_2$O$_4$; e NaOH, EtOH.

Reagents:
a DMF dimethylacetal, DMF, 100° C.; b aq Na$_2$S$_2$O$_4$ reflux.

Extension of this approach to the synthesis of 1 would require 11 (shown in Reaction Scheme 2) as starting material but it is difficult to obtain. Another approach that has been used to synthesize 7-substituted pyrrolo[3,2-d]pyrimidines such as 9-deazainosine utilized a 2-ethoxycarbonyl-3-aminopyrrole 12 which cyclized readily on treatment with formamidine acetate to give 13.[9] The same treatment applied to pyrrole 14 should produce 1 but 14 has not yet been reported. A useful synthesis of 4-substituted pyrrole 15 has been described[7] whereby the masked aldehyde ethyl (ethoxymethylene)cyanoacetate 16 was treated with diethyl aminomalonate 17 under basic conditions. However, when 3-ethoxyacrylonitrile was treated with 17 under the same conditions there was no sign of pyrrole 14 being formed. It is known[10] that isoxazole 18 will react under basic conditions to produce the unstable 3-oxopropionitrile 19 as a transient intermediate. We have found that treatment of 19 without isolation with 17 gave an intermediate presumed to be 20 as a stereoisomeric mixture. Further treatment of this with sodium ethoxide in ethanol produced pyrrole 14 in good overall yield. When 14 was allowed to react with formamidine acetate in refluxing ethanol the pyrrolo[3,2-d]pyrimidine 1 was formed in high yield. This new synthesis of 1 from isoxazole is facile and can be effected without recourse to chromatography. The ready availability of 14 in this way would also allow access to 2 by known methods[7,11] but the above route is superior in our experience.

The process according to this aspect of the invention also extends to the synthesis of other compounds of the formula (A) defined above in which Y is an unsubstituted or substituted alkyl or arylalkyl group having 1 to 8 carbon atoms. These compounds are novel and constitute a further aspect of the invention. Examples of suitable substituents for Y are F, Cl or OMe.

In general terms, the compounds of the formula (A) can be prepared by reacting isoxazole 18 with alkoxide ions in the presence of an alcohol, quenching the reaction with an acid, reacting the resulting reaction mixture with a dialkyl aminomalonate; isolating an organic phase of the resulting reaction mixture and reducing it to a residue, and reacting the residue with a base in a protic or aprotic solvent to produce a compound of the formula (A). It is generally preferred that this final step involves reaction with alkoxide ions in excess alcohol. When the compound 14 itself is to be prepared, the alcohol used in excess in this step is ethanol and the alkoxide ions are ethoxide ions (as shown in Reaction Scheme 2). Compounds of the formula (A) in which Y is other than ethyl can be prepared by selecting an appropriate alcohol corresponding to the desired group Y.

The compound 1 may be prepared from the compound of formula (A) thus prepared by reaction with a reagent capable of delivering a formyl equivalent. Conveniently, this reagent may be formamidine acetate although other suitable reagents will be apparent to those skilled in the art.

In conclusion, we have invented a synthesis of the previously unknown compounds of formula (A) from which the pyrrolopyrimidine 1 is now readily available. We have also invented a shorter synthetic approach to 2 so that it is much more readily available.

Reaction Scheme 2

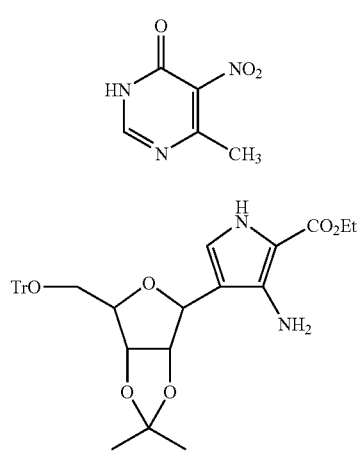

-continued

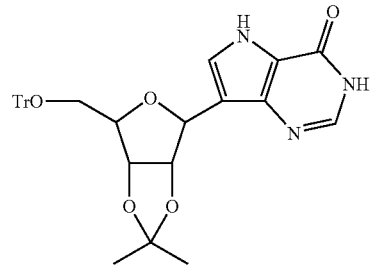

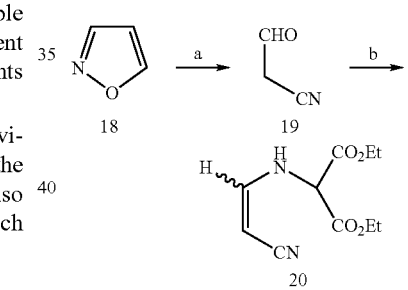

Reagents:
a NaOEt, EtOH, then HOAc quench; b 17, NaOAc;
c NaOEt, EtOH; d formamidine acetate, EtOH reflux.

The invention thus in a further embodiment also relates to a method of preparing the compound 3 or 4 defined above via the intermediate compound 3H,5H-pyrrolo[3,2-d]pyrimidin-4-one (1) or 2-amino-3H,5H-pyrrolo[3,2-d]pyrimidin4-one (2). The compound 3 or 4 can be prepared by first carrying out N,O-protection of the compound 1 or 2, brominating the protected compound, followed by lithiation of the resulting brominated compound, addition of the resulting Lithiated species to a protected imine, specifically a 2,3,5-tri-O-protected 1,N-dehydro-1,4-dideoxy-1,4-imino-D-ribitol, and N,O-deprotection of the resulting species to form the compound 3 or 4. Typically, the protecting groups used to protect the imine may be selected from trialkylsilyl, arylalkyl and isopropylidene groups. This synthetic route with preferred reagents to prepare the compound 3 is shown in Reaction Scheme 3. Other suitable reagents and reaction conditions for each stage of the synthesis will be apparent to those persons skilled in the art.

Reaction Scheme 3

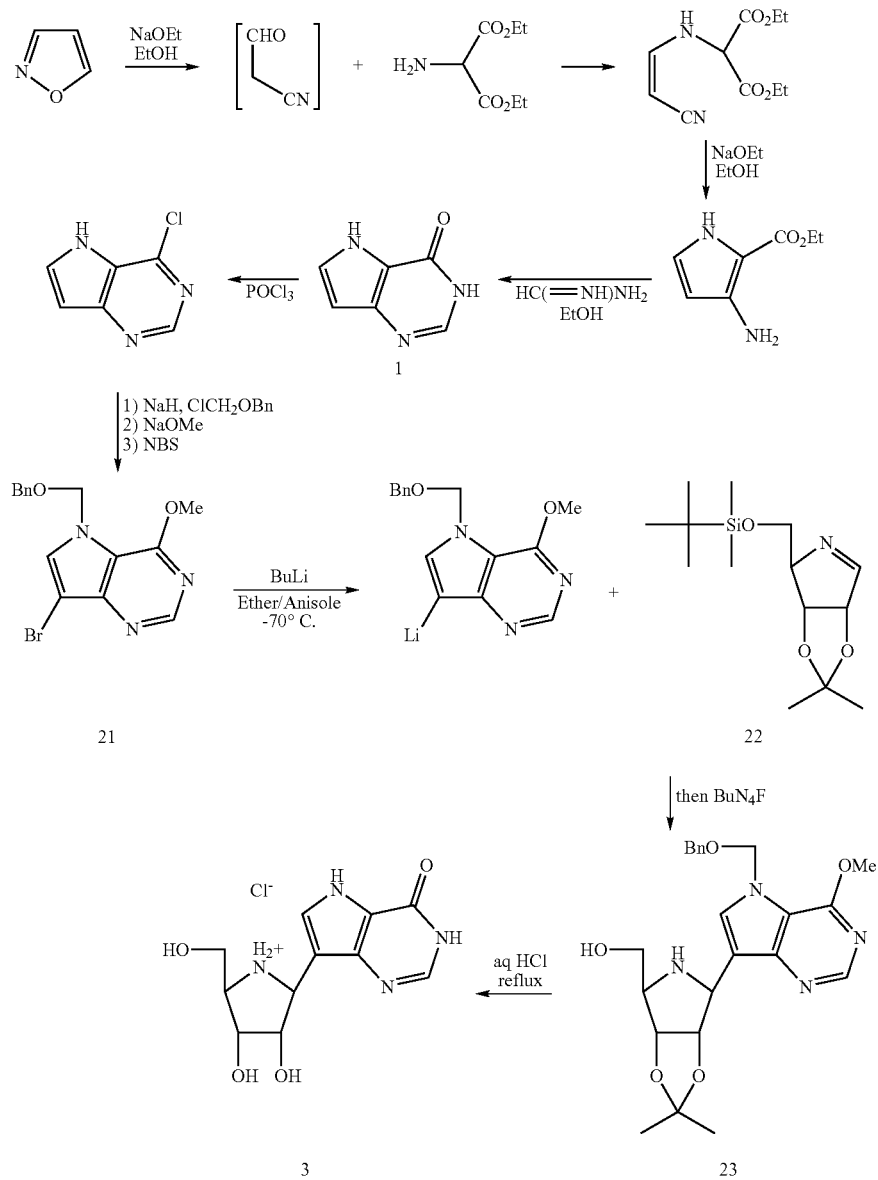

The invention will now be further described with reference to the following non-limiting examples.

EXAMPLES

NMR spectra were recorded on a Bruker AC-300 instrument at 300 MHz or 75 MHz ($^{13}$C). High resolution accurate mass determinations were performed on a VG70-250S mass spectrometer under chemical ionization conditions using isobutane or ammonia as the ionizing gas. Melting points were determined on a Reichert hot stage microscope and are uncorrected. Aluminium backed silica gel sheets (Merck or Reidel de Haen) were used for thin layer chromatography. Column chromatography was performed on silica gel (230-400 mesh, Merck). Chromatography solvents were distilled prior to use. Anhydrous solvents were obtained from Aldrich.

Example 1.1

2-(N-Dimethylaminomethylene)amino-6-(2-dimethylaminovinyl)-5-nitropyrimidin-4-one (10)

A mixture of $5^8$ (20 g) with dry DMF (250 ml) and DMF dimethylacetal (75 ml) was stirred at 100° C. for 24 h and then cooled. Acetone (500 ml) was added and the mixture was filtered and washed with acetone affording 10 as an orange/brown solid (26.3 g, 80%). Recrystallization from DMF gave an orange solid with mp >300° C. (dec). $^1$H NMR (d$^6$-DMSO), δ 8.59 (s, 1H), 7.81 (d, J=12.5 Hz, 1H), 5.30 (d, J=12.5 Hz, 1H), 3.12 (s, 3H), 3.00 (s, 3H), 2.93 (s, 6H). $^{13}$C NMR δ 168.4, 166.0, 159.2, 158.5, 149.5, 129.1, 90.6, 41.8, 35.7.

Example 1.2

2-Amino-3H,5H-pyrrolo[3,2-d]pyrimidin-4-one (2)

A mixture of 10 (24 g) and sodium dithionite (48 g) in water (240 ml) was heated under reflux for 2 h. The suspension was hot filtered, cooled and then filtered to give 2 (7.84 g, 61%) as a yellow/brown solid. Recrystallised from water it had mp >300° C. $^1$H NMR (d$^6$-DMSO), was as reported.[3] $^{13}$C NMR δ 155.9, 152.0, 146.6, 128.3, 113.6, 101.2.

Example 1.3

3-Amino-2-ethoxycarbonylpyrrole (14)

A solution of sodium ethoxide in ethanol (2M, 152 mL, 305 mmol) was added slowly to a stirred solution of isoxazole 18 (20 g, 290 mmol) in ethanol (80 mL) in an ice bath with the reaction temperature ≦8° C. After an additional 0.5 h with stirring, acetic acid (5.5 mL, 100 mmol), diethyl aminomalonate hydrochloride (40.9 g, 193 mmol) and sodium acetate (16.4 g, 200 mmol) were added and the mixture was stirred at room temperature for 2 days after which most of the ethanol was removed under vacuum. The residue was partitioned between chloroform and water and the organic phase was dried and filtered through a pad of silica gel. Evaporation afforded a syrup which was dissolved in a solution of sodium ethoxide in ethanol (0.5 M, 400 mL) and the solution was stirred at room temperature for 3 days. Acetic acid (12 mL, 210 mmol) was added and the ethanol removed under vacuum. The residue was dissolved in chloroform and washed with NaHCO$_3$ (aq., pH kept ~7) The organic phase was dried and filtered through a thick pad of silica gel to give crude syrupy 3-amino-2-ethoxycarbonylpyrrole (16.4 g, 106 mmol) with clean $^1$H and $^{13}$C NMR spectra that was suitable for synthetic use. A portion in ether was treated with HCl in dioxane to precipitate the corresponding hydrochloride salt. Recrystallized from ethyl acetate/ethanol it had mp 197-200° C.; $^1$H NMR (d$_6$-DMSO), δ 7.02 (t, J=3.0 Hz, 1H), 6.34 (t, J=2.5 Hz, 1H), 4.26 (q, J=7.1 Hz, 2H), 1.31 (t, J=7 Hz, 3H). $^{13}$C NMR δ 159.7, 123.2, 121.6, 114.7, 106.1, 60.6, 14.6. Anal. Calcd for C$_7$H$_{11}$ClN$_2$O$_5$: C, 44.10; H, 5.82; N, 14.70. Found: C, 44.02; H, 6.13; N, 14.55.

Example 2

3H,5H-Pyrrolo[3,2-d]pyrimidin-4-one (1)

Formamidine acetate (20 g, 0.19 mol.) was added to a solution of crude 2-ethoxycarbonyl-3-aminopyrrole (14) (15.3 g, 0.1 mol.) in ethanol (150 ml) and the solution was heated under reflux for 16 h and then cooled. The solid formed was filtered, washed with ethanol and dried to give 3H,5H-pyrrolo[3,2-d]pyrimidin-4-one (1) (11.5 g, 85.2 mmol.). Recrystallized from water it had mp >300° C. $^1$H NMR (d$^6$-DMSO), was as reported[3]. $^{13}$C NMR δ 154.0, 145.0, 141.8, 127.7, 118.2, 103.3.

Example 3

Preparation of (1S)-1,4-dideoxy-1-C-(4-hydroxy-pyrrolo[3,2-d]pyrimidin-7-yl)-1,4-imino-D-ribitol (3)

Example 3.1

5-N-Benzyloxymethyl-7-bromo-4-methoxypyrrolo [3,2-d]pyrimidine (21)

3H,5H-pyrrolo[3,2-d]pyrimidin-4-one (11.5 g), prepared according to Example 2, was converted into 4-chloropyrrolo [3,2-d]pyrimidine as described in Imai, K., *Chem. Pharm. Bull.*, 1964, 12, 1030-1042. A suspension of 4-chloropyrrolo [3,2-d]-pyrimidine (6.94 g) in dry tetrahydrofuran (100 ml) was stirred with cooling in an ice bath while sodium hydride (60%, 2.17 g, 1.2 eq) was added slowly. Then benzyl chloromethyl ether (7.1 ml) was added slowly with cooling and the resulting mixture was stirred at room temperature for 0.5 h. Methanol (25 ml) was added carefully and the resulting solution was cooled in an ice bath while sodium hydride (60%, 1.81 g) was added slowly and then allowed to warm to room temperature. The solvents were removed, the residue was dissolved in chloroform and washed with water, then processed normally. The crude product in methylene chloride (50 ml) was treated with N-bromosuccinimide (8.0 g) and the solution stirred at room temperature for 0.5 h. The solution was evaporated and chromatography of the residue afforded 5-N-benzyloxymethyl-7-bromo-4-methoxypyrrolo[3,2-d] pyrimidine (7.0 g). $^{13}$C NMR (CDCl$_3$), δ 156.8, 151.4, 148.8, 136.9, 131.9, 128.9, 128.5, 128.1, 116.0, 92.8, 77.6, 70.8, 54.2.

Example 3.2

5-O-tert-Butyldimethylsilyl-1,N-dehydro-1,4-dideoxy-1,4-imino-2,3-O-isopropylidene-D-ribitol (22)

A solution of 5-O-tert-butyldimethylsilyl-1,4-dideoxy-1,4-imino-2,3-O-isopropylidene-D-ribitol (Furneaux et al, *Tetrahedron* 53 (1997) 2915 and references therein) (4.5 g) in pentane (90 ml) was stirred with N-chlorosuccinimide (2.7 g) for 1 h. The solids and solvent were removed and the residue was dissolved in dry tetrahydrofuran (90 ml) and cooled to −78° C. A solution of lithium tetramethylpiperidide (56 ml, 0.4 M in tetrahydrofuran) was added slowly dropwise. Petroleum ether was then added and the solution was washed with water, dried and concentrated to dryness. The residue was chromatographed on silica gel eluted with 0.2% triethylamine and 30% ethyl acetate in hexanes to afford 5-O-tert-butyldimethylsilyl-1,N-dehydro-1,4-dideoxy-1,4-imino-2,3-O-isopropylidene-D-ribitol (3.66 g).

Example 3.3

(1S)-1-C-(5-N-Benzyloxymethyl-4-methoxypyrrolo [3,2-d]pyrimidin-7-yl)-1,4-dideoxy-1,4-imino-2,3-O-isopropylidene-D-ribitol (23)

A solution of the product from Example 3.1 (5.15 g) in anisole (60 ml) and ether (100 ml) was stirred and cooled to −70° C. whereupon some of the material reprecipitated. Butyllithium (1.4 M, 10.6 ml) was added slowly to the mixture and then after 0.25 h a solution of the product from Example 5.2 (2.1 g) in ether (10 ml) was added. The resulting solution was allowed to warm slowly to 0° C., and then was washed with water and processed normally. The crude product in tetrahydrofuran (20 ml) was stirred with 1M tetrabutylammonium fluoride in is tetrahydrofuran (15 ml) for 1 h and then evaporated. The residue in toluene (60 ml) was washed with water (×2) and processed normally. Chromatography of the residue afforded 1-(S)-1-C-(5-N-benzyloxymethyl-4-methoxypyrrolo[3,2-d]pyrimidine-7-yl)-1,4-dideoxy-1,4-imino-2,3-O-isopropylidene-D-ribitol (2.1 g). $^{13}$C NMR (CDCl$_3$), δ 156.8, 150.1, 149.2, 137.2, 130.9, 128.8, 128.3, 128.0, 118.3, 117.1, 113.1, 86.1, 83.9, 77.3, 70.6, 64.7, 64.6, 62.5, 54.0, 28.2, 25.8.

Example 3.4

(1S)-1,4-Dideoxy-1-C-(4-hydroxypyrrolo[3,2-d]
pyrimidin-7-yl)-1,4-imino-D-ribitol (3)

A solution of the product from Example 3.3 (1.57 g) in concentrated HCl (30 ml) was heated under reflux for 1 h, and then concentrated to dryness. Chromatography of the residue ($CH_2Cl_2$/MeOH/aq $NH_3$ 5:4:1) afforded 1,4-dideoxy-(1S)-1-C-(4-hydroxypyrrolo[3,2-d]pyrimidin-7-yl)-1,4-imino-D-ribitol (0.94 g) as the free base. NMR (300 MHz, $D_2O$ with DCl, δ ppm): $^{13}C$ (relative to internal acetone at 33.2 ppm), 58.1 (C-1'), 61.4 (C-5'), 68.8 (C-4'), 73.3 (C-3'), 76.7 (C-2'), 107.5 (q), 121.4 (q), 133.5 (C-2), 135.0 (q), 148.0 (C-6), and 155.4 (q); $^1H$ (relative to internal acetone at 2.20 ppm), 3.90 (H-4'), 3.96 (m, H-5',5''), 4.44 (dd, H-3', $J_{2',3'}$ 5.4 Hz, $J_{3',4'}$ 3.2 Hz), 4.71 (dd, $J_{1',2'}$ 9.0 Hz, H-2'), 5.00 (d, H-1'), 8.00 (s, H-6), and 9.04 (s, H-2).

Example 4

Preparation of (1S)-1,4-dideoxy-1-C-(2,4-dihydroxy-pyrrolo[3,2-d]pyrimidin-7-yl)-1,4-imino-D-ribitol

Example 4.1

2,4-Dibenzyloxypyrrolo[3,2-d]pyrimidine was prepared by the method used for the preparation of 2,4-dimethoxypyrrolo[3,2-d]pyrimidine as described in Cupps, T. L., Wise, D. S. and Townsend, L. B. *J. Org. Chem.*, 1983, 48, 1060-1064 and references therein. A solution of sodium benzoxide was prepared by adding sodium (4.5 g) to benzyl alcohol (100 ml) and heating under argon with stirring until all the sodium had reacted. This was added slowly to a solution of 2,4-dichloro-6-methyl-5-nitropyrimidine (17 g) in benzyl alcohol (80 ml). When the exothermic reaction was complete, ether (500 ml) was added and the resulting solution was washed with water, dried ($MgSO_4$), and evaporated, excess benzyl alcohol being removed by distillation under high vacuum. Dimethylformamide dimethyl acetal (25 ml) was added to a solution of the crude residue in dry DMF (100 ml). The resulting solution was heated at 100° C. for 3 h, then evaporated to dryness under high vacuum. The solid residue was triturated with hot ethanol, cooled and filtered to yield 2,4-dibenzyloxy-6-(2-dimethylaminoethenyl)-5-nitropyrimidine as an orange solid (24.5 g). A suspension of this product (20 g) in acetic acid (300 ml) was stirred with zinc dust (30 g), the reaction being cooled in an ice-bath during an exothermic reaction, when the reaction temperature rose to 50° C. The reaction mixture was allowed to attain room temperature for 2 h, and was then filtered, evaporated and partitioned between chloroform and aqueous bicarbonate. The organic phase was washed with water, dried ($MgSO_4$) and evaporated to give 2,4-dibenzyloxypyrrolo[3,2-d]pyrimidine as a solid (15.2 g).

Example 4.2

Crude 2,4-dibenzyloxpyrrolo[3,2-d]pyrimidine from Example 4.1 (2.0 g) in dry tetrahydrofuran (40 ml) was stirred with excess sodium hydride (0.5 g, 60% in oil) and tert-butyldimethylsilyl chloride (1.37 g) was added. After 30 min, the reaction mixture was quenched with water and partitioned between ether and water. The organic phase was dried ($MgSO_4$) and evaporated to give an N-tert-butyldimethylsilyl derivative. This was dissolved in dichloromethane (40 ml) and treated portionwise with N-bromosuccinimide (ca. 0.8 g) until the starting material had been fully converted to the corresponding bromo-derivative as judged by TLC (silica gel, ethyl acetate-hexanes, 1:10 v/v). The solution was washed with water then saturated aqueous sodium bicarbonate and dried ($MgSO_4$), and the product was isolated by chromatography on silica gel (eluted with EtOAc-hexanes, 1:10 v/v) to afford 7-bromo-5-N-tert-butyldimethylsilyl-2,4-dibenzyloxypyrrolo[3,2-d]pyrimidine as a white solid (1.80 g).

Example 4.3

A solution of 7-bromo-5-N-tert-butyldimethylsilyl-2,4-dibenzyloxypyrrolo[3,2-d]pyrimidine (0.786 g) from Example 39.2 in anisole (20 ml) and ether (30 ml) was stirred and cooled to −70° C. under argon. Butyllithium (1.4M in hexanes, 2.5 ml) was added slowly to the mixture and then after 0.25 h a solution of 5-O-tert-butyldimethylsilyl-1,N-dehydro-1,4-dideoxy-1,4-imino-2,3-O-isopropylidene-D-ribitol (0.215 g), prepared from 5-O-tert-butyldimethylsilyl-1,4-dideoxy-1,4-imino-2,3-O-isopropylidene-D-ribitol (0.30 g) as described in Example 3.2, in ether (2 ml) was added. The resulting solution was allowed to warm slowly to 15° C., and then was washed with water, dried ($MgSO_4$) and evaporated. The product (0.225 g) was isolated by chromatography on silica gel (eluted with ethyl acetate-hexanes, 1:3 to 1:2 v/v).

Example 4.4

The product from Example 4.3 (0.10 g) was subjected to hydrogenolysis in ethanol (5 ml) over palladium on charcoal (10%, 50 mg) at atmospheric pressure. After 2 h, the reaction mixture was filtered, evaporated and the residue chromatographed on silica gel (eluted with ethyl acetate-hexanes, 1:1 v/v) afforded (1S)-5-O-tert-butyl-dimethylsilyl-1-C-(5-N-tert-butyldimethylsilyl-2,4-dihydroxypyrrolo[3,2-d]pyrimidine-7-yl)-1,4-dideoxy-1,4-imino-2,3-O-isopropylidene-D-ribitol as a white crystalline solid (0.058 g).

Example 4.5

The product from Example 4.4 (0.058 g) was dissolved in methanol (5 ml), conc. hydrochloric acid (1 ml) was added, and the solution was allowed to stand overnight at room temperature, at which stage some solid had crystallised. The reaction mixture was evaporated to a solid residue and this was extracted twice with ether, triturated with ethanol and filtered to give (1S)-1.4-dideoxy-1-C-(2.4-dihydroxypyrrolo[3,2-d]pyrimidin-7-yl)-1,4-imino-D-ribitol hydrochloride salt as a white crystalline solid (0.025 g). $^{13}C$ NMR ($D_2O$, δ relative to acetone at 33.17 ppm), 159.7, 155.7, 137.0, 131.3, 114.2, 104.1, 76.2, 73.6, 68.4, 61.6 and 58.5 ppm.

Example 5

5-N-Benzyloxymethyl-7-bromo-4-tert-butoxypyrrolo[3,2-d]pyrimidine

A suspension of 4-chloropyrrolo[3,2-d]pyrimidine (5.0 g) in tetrahydrofuran (100 mL) was treated with sodium hydride and benzyl chloromethyl ether as described in Example 3.1. Dry N,N-dimethylformamide (20 mL) and tert-butanol (20 mL) were added followed by more sodium hydride (2.0 g, 60% dispersion) and the resulting mixture was stirred at room temperature for 16 h, then partitioned between chloroform and water. The organic phase was processed normally and the crude product was treated with N-bromosuccinimide and isolated as described for the equivqlent product in Example 3.1 to give 5-N-benzyloxymethyl-7-bromo-4-tert-butoxypyrrolo[3,2-d]pyrimidine (5.8 g) as a solid. $^{13}$C NMR (CDCl$_3$), δ 156.3, 151.1, 148.7, 137.1, 131.4, 128.9, 128.4, 127.8, 117.0, 92.6, 84.0, 77.6, 70.5, 29.0.

Example 6

4-Benzyloxy-5-N-benzyloxymethyl-7-bromopyrrolo[3,2-d]pyrimidine

A suspension of 4-chloropyrrolo[3,2-d]pyrimidine (2.0 g) in tetrahydrofuran (25 mL) was treated with sodium hydride and benzyl chloromethyl ether as described in Example 3.1. Benzyl alcohol (4 mL) was added followed by more sodium hydride (0.8 g, 60% dispersion) and the resulting mixture was stirred at room temperature for 3 h, then partitioned between chloroform and water. The organic phase was processed normally and the benzyl alcohol was distilled off under high vacuum (bath temperature 150° C.). The crude residue was treated with N-bromosuccinimide and isolated as described in Example 3.1 to give 4-benzyloxy-5-N-benzyloxymethyl-7-bromopyrrolo[3,2-d]pyrimidine (2.27 g) as a solid. $^{13}$C NMR (CDCl$_3$), δ 156.3, 151.3, 149.1, 137.0, 136.3, 132.1, 129.1, 128.8, 128.7, 128.4, 127.9, 115.9, 92.7, 78.0, 71.0, 68.8.

Example 7

7-Bromo-4-methoxy-5-N-(2-trimethylsilylethoxy)methylpyrrolo[3,2-d]pyrimidine

4-Chloropyrrolo[3,2-d]pyrimidine (2.0 g) was treated as described in Example 3.1 except that (2-trimethylsilylethoxy)methyl chloride was used in place of benzyl chloromethyl ether, to give 7-bromo-4-methoxy-5-N-(2-trimethylsilylethoxy)methylpyrrolo[3,2-d]pyrimidine (2.0 g) as a solid. $^{13}$C NMR (CDCl$_3$), δ 156.8, 151.3, 148.8, 132.0, 115.9, 92.4, 78.2, 66.7, 54.2, 18.1, −1.1.

Example 8

4-Benzyloxy-7-bromo-5-N-(2-trimethylsilylethoxy)methylpyrrolo[3,2-d]pyrimidine

4-Chloropyrrolo[3,2-d]pyrimidine (2.0 g) was treated as described in Example 6 except that (2-trimethylsilylethoxy)methyl chloride was used in place of benzyl chloromethyl ether to give 4-benzyloxy-7-bromo-5-N-(2-trimethylsilylethoxy)methylpyrrolo[3,2-d]pyrimidine (1.43 g) as a solid. $^{13}$C NMR (CDCl$_3$), δ 156.2, 151.3, 149.1, 136.4, 132.1, 129.0, 128.8, 128.6, 115.8, 92.5, 78.1, 68.8, 66.6, 18.1, −1.1.

Example 9

5-N-Allyl-7-bromo-4-methoxypyrrolo[3,2-d]pyrimidine

4-Chloropyrrolo[3,2-d]pyrimidine (1.0 g) was treated as described in Example 3.1 except that allyl bromide was used in place of benzyl chloromethyl ether to give 5-N-allyl-7-bromo-4-methoxypyrrolo[3,2-d]pyrimidine (1.1 g) as a solid. $^{13}$C NMR (CDCl$_3$), δ 156.8, 150.9, 148.1, 133.8, 131.6, 118.5, 115.9, 90.6, 54.1, 52.2.

Example 10

Preparation of 4-benzyloxy-2-N-formylaminopyrrolo[3,2-d]pyrimidine

Example 10.1

2-N-Acetyl-6-methyl-5-nitropyrimidin-4-one

A suspension of 2-amino-6-methyl-5-nitropyrimidin-4-one (G. N. Mitchell et. al. *J. Org. Chem.*, 1974, 39, 176) (20.0 g) in acetic anhydride (120 mL) was heated under reflux for 0.5 h. The cooled suspension was filtered and the solids washed with ether to give 2-N-acetyl-6-methyl-5-nitropyrimidin-4-one (19.7 g). $^{13}$C NMR (d$_6$-DMSO), δ 174.5, 161.9, 153.3, 150.9, 133.8, 24.2, 21.4.

Example 10.2

2-Amino-4-benzyloxy-6-methyl-5-nitropyrimidine

A suspension of 2-N-acetyl-6-methyl-5-nitropyrimidin-4-one (10 g) in phosphoryl chloride (100 mL) and N,N-diethylaniline (10 mL) was heated under gentle reflux for 5 mins. The cooled solution was concentrated and a solution of the residue in chloroform (300 mL) was washed with water, aq NaHCO$_3$, then dried and concentrated to dryness to give a dark red/brown solid (14.3 g). A solution of this material in benzyl alcohol (30 mL) was added to sodium benzyloxide in benzyl alcohol [prepared by adding sodium (2.2 g) to benzyl alcohol (50 mL)]. After 1 h chloroform (500 mL) was added and the solution was processed normally followed by evaporation of the excess benzyl alcohol under high vacuum (bath temperature 150° C.). A solution of the residue in chloroform was filtered through a plug of silica gel and concentrated to give 2-amino-4-benzyloxy-6-methyl-5-nitropyrimidine (11.0 g) as a solid. $^{13}$C NMR (d$_6$-DMSO), δ 164.2, 162.0, 161.7, 136.1, 128.8, 128.5, 128.2, 125.4, 68.3, 22.0.

Example 10.3

4-Benxyloxy-2-[(N,N-dimethylamino)methylene]amino-6-[(2-N,N-dimethylamino)vinyl]-5-nitropyrimidine A solution of 2-amino-4-benzyloxy-6-methyl-5-nitropyrimidine (5.9 g) in N,N-dimethylformamide (40 mL) and N,N-dimethylformamide dimethyl acetal (15 mL) was heated at 80° C. for 2 d. After cooling, ether (200 mL) was added and the mixture was filtered and washed with ether to give 4-benxyloxy-2-[(N,N-dimethylamino)methylene]amino-6-[(2-N,N-dimethylamino)vinyl]-5-nitropyrimidine (6.9 g) as an orange solid. $^{13}$C NMR (CDCl$_3$), δ 164.1, 162.4, 160.5, 159.8, 151.6, 136.9, 128.8, 128.2, 127.6, 123.6, 83.5, 41.7, 35.7. Anal. calc. for C$_{18}$H$_{22}$N$_6$O$_3$: C, 58.37; H, 5.99; N, 22.69. Found: C, 58.02; H, 5.97; N, 22.83.

Example 10.4

4-Benzyloxy-2-N-formylaminopyrrolo[3,2-d]pyrimidine

4-Benxyloxy-2-[(N,N-dimethylamino)methylene]amino-6-[(2-N,N-dimethylamino)vinyl]-5-nitropyrimidine (2.8 g) was added to a solution of sodium dithionite (5.6 g) in water (50 mL) followed by ethanol (25 mL) and the mixture was heated under reflux for 5 mins. Water (50 mL) was added to the resulting solution and after cooling the white precipitate was filtered, washed with water and dried to give 4-benzyloxy-2-N-formylaminopyrrolo[3,2-d]pyrimidine (1.73 g). $^{13}$C NMR (d$_6$-DMSO), δ 163.8, 155.7, 151.4, 150.3, 136.8, 131.5, 128.8, 128.5, 112.2, 101.2, 67.7.

Example 11

Preparation of 4-benzyloxy-5-N-benzyloxymethyl-7-bromo-2-bis(4-methoxybenzyl)aminopyrrolo[3,2-d]pyrimidine Example 11.1

2-Amino-4-benzyloxy-5-N-benzyloxymethylpyrrolo[3,2-d]pyrimidine

Sodium hydride (1.88 g, 60% dispersion) was added to a solution of 4-benzyloxy-2-N-formylaminopyrrolo[3,2-d]pyrimidine (4.2 g) (Example 10) in tetrahydrofuran (200 mL) followed by chloromethyl benzyl ether (2.5 mL). After 1 h the mixture was quenched carefully with water and concentrated to dryness. A solution of the residue in methanol (150 mL) and 1M aq NaOH (50 mL) was heated under reflux for 0.5 h, cooled, and partitioned between chloroform and water. The organic phase was processed normally followed by chromatography to give 2-amino-4-benzyloxy-5-N-benzyloxymethylpyrrolo[3,2-d]pyrimidine (4.16 g) as a white solid. $^{13}$C NMR (CDCl$_3$), δ 158.2, 157.1, 154.1, 137.6, 137.0, 133.2, 128.9, 128.8, 128.5, 128.2, 128.0, 111.5, 102.4, 77.6, 70.4, 68.0.

Example 11.2

2-Amino-4-benzyloxy-5-N-benzyloxymethyl-7-bromopyrrolo[3,2-d]pyrimidine

A solution of 2-amino-4-benzyloxy-5-N-benzyloxymethylpyrrolo[3,2-d]pyrimidine (1.0 g) in methylene chloride (30 mL) was stirred in an ice bath while N-bromosuccinimide (0.5 g) was added portion-wise. The solution was concentrated and chromatography afforded 2-amino-4-benzyloxy-5-N-benzyloxymethyl-7-bromopyrrolo[3,2-d]pyrimidine (1.15 g) as a white solid. $^{13}$C NMR (CDCl$_3$), δ 158.8, 157.2, 150.9, 137.3, 136.6, 131.8, 129.0, 128.8, 128.6, 128.5, 128.3, 127.9, 111.3, 90.3, 77.8, 70.7, 68.4.

Example 11.3

4-Benzyloxy-5-N-benzyloxymethyl-7-bromo-2-{N,N-bis(4-methoxybenzyl)amino}pyrrolo[3,2-d]pyrimidine Sodium hydride (0.6 g, 50% dispersion) was added to a stirred solution of 2-amino-4-benzyloxy-5-N-benzyloxymethyl-7-bromopyrrolo[3, 2-d]pyrimidine (1.2 g) in N,N-dimethylformamide (25 mL) followed by 4-methoxybenzyl chloride (1.1 mL). After 1 h the reaction was quenched carefully with water, chloroform was added and the solution was washed (×2) with water. Normal processing followed by chromatography afforded 4-benzyloxy-5-N-benzyloxymethyl-7-bromo-2-{N,N-bis-(4-methoxybenzyl)amino}pyrrolo[3,2-d]pyrimidine (1.7 g) as a white solid. $^{13}$C-NMR (CDCl$_3$), δ 159.0, 158.5, 156.5, 151.5, 137.4, 137.0, 131.8, 131.6, 129.7, 128.9, 128.8, 128.4, 128.3, 128.0, 114.1, 110.5, 91.1, 77.8, 70.6, 68.0, 55.7, 49.4. Anal. calc. for C$_{37}$H$_{35}$BrN$_4$O$_4$: C, 65.39; H, 5.19; Br, 11.76; N, 8.24. Found: C, 65.47; H, 5.17; Br, 11.55; N, 8.42.

Example 12

Preparation of 5-N-benzyl-4-benzyloxy-7-bromo-2-N,N-dibenzylaminopyrrolo[3,2-d]pyrimidine A suspension of the product from Example 10.4 (1.5 g) in methanol (25 mL) and 1M aq NaOH (10 mL) was heated under reflux for 0.5 h and then concentrated to dryness. Trituration with water gave crystalline 2-amino-4-benzyloxypyrrolo[3,2-d]pyrimidine (1.16 g). Sodium hydride (0.7 g, 50% dispersion) was added to a solution of a portion (0.5 g) of the above material in N,N-dimethylformamide (15 mL) followed by benzyl bromide (0.96 mL). After 6 h the solution was processed as described in Example 11.3. A solution of the product in methylene chloride (25 mL) was stirred in an ice bath while N-bromosuccinimide (0.3 g) was added slowly. The solution was concentrated and chromatography afforded 5-N-benzyl-4-benzyloxy-7-bromo-2-N,N-dibenzylaminopyrrolo[3,2-d]pyrimidine (0.65 g) as a solid. $^{13}$C NMR (CDCl$_3$), δ 158.3, 156.6, 150.8, 139.8, 138.0, 136.9, 131.6, 129.1, 128.8, 128.7, 128.4, 128.3, 128.1, 127.4, 127.2, 110.8, 88.9, 67.9, 53.3, 50.2.

Example 13

Preparation of 4-benzyloxy-5-N-benzyloxymethyl-7-bromo-2-fluoropyrrolo[3,2-d]pyrimidine A solution of the product from Example 11.2 (0.9 g) in dry pyridine (40 mL) was cooled in an ice bath while hydrogen fluoride-pyridine (~65%) (15 mL) was added slowly keeping the temperature ≦10° C. The resulting solution was cooled to 0° C., tert-butyl nitrite (3 mL) was added, and the solution was stirred in the ice bath for 3 h and then poured carefully onto saturated aq NaHCO$_3$ (500 mL) adding Na$_2$CO$_3$ as required to keep the solution basic. The mixture was extracted (×2) with chloroform which was dried and concentrated to dryness. Chromatography gave 4-benzyloxy-5-N-benzyloxymethyl-7-bromo-2-fluoropyrrolo[3,2-d]pyrimidine (0.63 g) as a solid. $^{13}$C NMR (CDCl$_3$), δ 158.5 (J$_{C,F}$=17 Hz), 157.5 (J$_{C,F}$=213 Hz), 150.6 (J$_{C,F}$=16 Hz), 136.8, 135.5, 133.9, 129.1, 128.9, 128.9, 128.5, 127.9, 114.1, 91.9, 77.9, 71.1, 70.0.

Example 14

Preparation of 4-benzyloxy-7-bromo-5-N-tert-butyldimethylsilyl-2-fluoropyrrolo[3,2-d]pyrimidine A solution of 2-amino-4-benzyloxypyrrolo[3,2-d]pyrimidine (0.85 g) (Example 12) in dry pyridine (20 mL) was treated with hydrogen fluoride-pyridine and tert-butyl nitrite as described in Example 13. A solution of the crude product in tetrahydrofuran (30 mL) was cooled in an ice bath while N-bromosuccinimide (0.6 g) was added portion-wise. The solution was concentrated and chromatography afforded 4-benzyloxy-7-bromo-2-fluoropyrrolo[3,2-d]pyrimidine (0.8 g) as a solid. A solution of this material (0.74 g) in tetrahydrofuran (30 mL) was cooled in an ice b a t h while sodium hydride (0.11 g, 60% dispersion) and then tert-butyldimethylsilyl chloride (0.41 g) were added. After 1 h methylene chloride (50 mL) was added and the reaction was quenched with water, then washed with additional water. Normal processing and chromatography afforded 4-benzyloxy-7-bromo-5-N-tert-butyldimethylsilyl-2-fluoropyrrolo[3,2-d]pyrimidine (0.82 g) as a solid. $^{13}$C NMR (CDCl$_3$), δ

158.4 (J$_{C,F}$=17 Hz), 157.5 (J$_{C,F}$=212 Hz), 153.5 (J$_{C,F}$=16 Hz), 137.7, 134.9, 130.5, 129.4, 129.0, 118.0, 93.3, 70.3, 26.6, 19.2, −1.9, −2.3.

Example 15

General Method for the Condensation of Lithiated pyrrolo[3,2-d]pyrimidines with 5-O-tert-butyldimethylsilyl-1,N-dehydro-1,4-dideoxy-1,4-imino-2,3-O-isopropylidene-D-ribitol A solution of the protected 7-bromopyrrolo[3,2-d]pyrimidine (chosen from Examples 5-14; xmmol.) in dry anisole (~4×mL) and dry ether (~8×mL) was cooled to −70° C. and butyl lithium (~1.5-2.5 M in hexanes) was added dropwise until t.l.c. examination indicated that the 7-bromopyrrolo[3,2-d]pyrimidine had been fully lithiated. A solution of 5-O-tert-butyldimethylsilyl-1,N-dehydro-1,4-dideoxy-1,4-imino-2,3-O-isopropylidene-D-ribitol (Example 3.2) (0.65-0.85×mmol.) in dry ether (0.5×mL) was added and the resulting solution was allowed to warm slowly to −10 to 10° C. The reaction was monitored by t.l.c. and quenched with water when no further reaction was observed. After washing with water the organic phase was dried, concentrated to dryness and then chromatography afforded the corresponding (1S)-5-O-tert-butyldimethylsilyl-1,4-dideoxy-1,4-imino-2,3-O-isopropylidene-1-C-pyrrolo[3,2-d]pyrimidin-7-yl-D-ribitol. In some instances this material was treated with either tetrabutylammonium fluoride in tetrahydrofuran or di-tert-butyl dicarbonate in methylene chloride followed by chromatography to facilitate purification and the corresponding (1S)-1,4-dideoxy-1,4-imino-2,3-O-isopropylidene-1-C-pyrrolo[3,2-d]pyrimidin-7-yl-D-ribitol or (1S)-N-tert-butoxycarbonyl-5-O-tert-butyldimethylsilyl-1,4-dideoxy-1,4-imino-2,3-O-isopropylidene-1-C-pyrrolo[3,2-d]pyrimidin-7-yl-D-ribitol were obtained.

The following compounds were prepared in this fashion:

(a) (1S)-5-O-tert-Butyldimethylsilyl-1,4-dideoxy-1,4-imino-2,3-isopropylidene-1-C-{4-methoxy-5-N-(2-trimethylsilyl)ethoxymethylpyrrolo[3,2-d]pyrimidin-7-yl}-D-ribitol as a syrup: $^{13}$C NMR (CDCl$_3$), δ 156.5, 150.1, 150.0, 131.0, 116.6, 116.5, 114.8, 86.8, 82.7, 77.7, 66.5, 66.3, 62.9, 61.9, 53.8, 23.0, 26.2, 25.9, 18.7, 18.1, 1.1, −5.1.

(b) (1S)-1-C-(5-N-Allyl-4-methoxypyrrolo[3,2-d]pyrimidin-7-yl)-1,4-dideoxy-1,4-imino-2,3-O-isopropylidene-D-ribitol as a syrup: $^{13}$C NMR (CDCl$_3$), δ 156.8, 149.6, 148.3, 134.2, 130.8, 118.1, 116.3, 113.2, 86.2, 83.7, 64.8, 64.4, 62.5, 53.9, 51.7, 28.2, 25.8.

(c) (1S)-1-C-(4-Benzyloxy-5-N-tert-butyldimethylsilyl-2-fluoropyrrolo[3,2-d]pyrimidin-7-yl)-5-O-tert-butyldimethylsilyl-1,4-dideoxy-1,4imino-2,3-O-isopropylidene-D-ribitol as a syrup: $^{13}$C NMR (CDCl$_3$), δ (157.7, 157.4, 154.8, 154.4, 154.2) representing three carbons with unresolved coupling to fluorine, 137.0, 134.9, 130.0, 128.9, 128.7, 128.6, 118.4, 116.5, 114.6, 85.8, 82.2, 69.4, 65.8, 62.1, 61.2, 27.7, 26.3, 25.9, 25.6, 18.8, 18.3, −2.6, −5.5.

(d) (1S)-1-C-(4-Benzyloxy-5-N-benzyloxymethyl-2-fluoropyrrolo[3,2-d]pyrimidin-7-yl)-5-O-tert-butyldimethylsilyl-1,4-dideoxy-1,4-imino-2,3-O-isopropylidene-D-ribitol as a syrup: $^{13}$C NMR (CDCl$_3$), δ 158.0 (J$_{C,F}$=17 Hz), 156.7 (J$_{C,F}$=214 Hz), 151.6 (J$_{C,F}$=16 Hz), 137.1, 135.9, 133.1, 129.1, 128.9, 128.8, 128.7, 128.3, 127.8, 116.6, 114.9, 86.3, 82.6, 77.6, 70.8, 69.4, 66.4, 63.1, 61.5, 28.0, 26.3, 25.9, 18.7.

(e) (1S)-1-C-{4-Benzyloxy-5-N-(2-trimethylsilylethoxy)methylpyrrolo[3,2-d]pyrimidin-7-yl}-N-tert-butoxycarbonyl-5-O-tert-butyldimethylsilyl-1,4-dideoxy-1,4-imino-2,3-O-isopropylidene-D-ribitol as a syrup: $^{13}$C NMR (C$_6$D$_6$, 70° C.) δ 157.5, 156.1, 151.5, 151.0, 138.6, 135.4, 118.3, 117.6, 113.2, 85.9, 85.4, 80.9, 79.1, 69.4, 69.1, 67.4, 64.8, 63.2, 61.3, 30.0, 29.2, 27.6, 27.1, 19.4, 1.3, −3.5, −3.6.

(f) (1S)-1-C-(4-Benzyloxy-5-N-benzyloxymethylpyrrolo[3,2-d]pyrimidin-7-yl)-N-tert-butoxycarbonyl-5-O-tert-butyldimethylsilyl-1,4-dideoxy-1,4-imino-2,3-O-isopropylidene-D-ribitol as a syrup: $^{13}$C NMR (C$_6$D$_6$), δ 156.0, 154.6, 150.1, 149.4, 137.6, 137.0, 135.0, 115.7, 111.8, 84.2, 83.8, 79.5, 77.3, 70.2, 67.8, 67.5, 63.1, 61.6, 28.5, 27.7, 26.2, 25.5, 18.6, −4.9.

(g) (1S)-1-C-(5-N-Benzyloxymethyl-4-tert-butoxypyrrolo[3,2-d]pyrimidin-7-yl)-N-tert-butoxycarbonyl-5-O-tert-butyldimethylsilyl-1,4-dideoxy-1,4-imino-2,3-O-isopropylidene-D-ribitol as a syrup: $^{13}$C NMR (C$_6$D$_6$), δ 156.2, 154.6, 149.8, 149.2, 137.8, 134.6, 115.5, 111.8, 84.2, 83.9, 82.3, 79.4, 77.0, 69.8, 67.5, 63.1, 61.6 28.6, 28.5, 27.7, 26.2, 25.5, 18.6, −4.9.

(h) (1S)-1-C-(5-N-Benzyl-4-benzyloxy-2-N,N-dibenzylaminopyrrolo[3,2-d]pyrimidin-7-yl)-5-O-tert-butyldimethylsilyl-1,4-dideoxy-1,4-imino-2,3-O-isopropylidene-D-ribitol as a syrup: $^{13}$C NMR (CDCl$_3$), δ 155.9, 155.0, 150.2, 138.6, 137.1, 135.8, 129.7, 127.6, 127.3, 126.9, 126.7, 126.5, 126.1, 125.6, 112.9, 111.8, 110.0, 84.6, 81.5, 66.1, 65.2, 62.4, 60.3, 51.4, 49.1, 26.5, 25.0, 24.2, 17.4.

(i) (1S)-1-C-{4-Benzyloxy-5-N-benzyloxymethyl-2-N,N-bis-(4-methoxybenzyl)aminopyrrolo[3,2-d]pyrimidin-7-yl}-N-tert-butoxycarbonyl-5-O-tert-butyldimethylsilyl-1,4-dideoxy-1,4-imino-2,3-O-isopropy a syrup: $^{13}$C NMR (CDCl$_3$), δ 158.9, 157.6, 156.3, 152.5, 137.8, 137.3, 132.0, 131.0, 129.1, 128.8, 128.7, 128.3, 128.1, 127.9, 114.4, 114.1, 111.2, 85.9, 82.8, 77.6, 70.4, 67.6, 66.6, 63.8, 61.5, 55.6, 49.6, 27.9, 26.4, 25.6, 18.8, −4.9.

REFERENCES (1) Miles, R. W.; Tyler, P. C.; Furneaux, R. H.; Bagdassarian, C. K.; Schramm, V. L. *Biochemistry,* 1998, 37, 8615-8621.
(2) Amarnath, V.; Madhav, R. *Synthesis,* 1974, 837-859.
(3) Imai, K. *Chem. Pharm. But.,* 1964, 12, 1030-1042.
(4) Brakta, M.; Doyle Daves, Jr, G. *J. Chem. Soc. Perkin Trans.* 1, 1992, 1883-1884.
(5) Kline, R. S.; Lim, M-I.; Tam, S. Y-K.; Fox, J. J. *J. Org. Chem.,* 1978, 43, 2536-2539.
(6) Taylor, E. C.; Young, W. B.; Ward, C. C. *Tetrahedron Lett,* 1993, 34, 4595-4598.
(7) Elliott, A. J.; Montgomery, J. A.; Walsh, D. A. *Tetrahedron Lett,* 1996, 37, 4339-4340.
(8) Mitchell, G. N.; McKee, R. L. *J. Org. Chem.,* 1974, 39, 176-179.
(9) Lim, M-I.; Ren, W-Y.; Otter, B. A.; Klein, R. S. *J. Org. Chem.,* 1983, 48, 780-788.
(10) Ciller, J. A.; Martin, N.; Seoane, C.; Soto, J. L. *J. Chem. Soc. Perkin Trans.* 1, 1985, 2581-2584.
(11) Elliott, A. J.; Morris, Jr., P. E.; Petty, S. L.; Williams, C. H. *J. Org. Chem.,* 1997, 62, 8071-8075.

INDUSTRIAL APPLICATION

The present invention provides a convergent synthetic route for preparing the inhibitors of purine nucleoside phosphorylase of the Formula (I). It is believed that this method will facilitate synthesis of those compounds.

Also provided are new intermediate compounds of the formula (XX) that are useful in the convergent synthesis.

The invention also provides new and improved methods of preparing 3H,5H-pyrrolo[3,2-d]pyrimidin-4-one and its 2-amino derivative, which are compounds useful in preparing

The invention claimed is:

1. A process of preparing the compound 3H,5H-pyrrolo[3,2-d]pyrimidin-4-one, comprising the step of reacting a reagent capable of delivering a formyl equivalent with a compound of the formula (A)

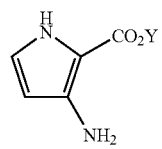

(A)

wherein Y is an unsubstituted or substituted alkyl or arylalkyl group having 1 to 8 carbon atoms.

2. The process as claimed in claim 1 wherein the reagent capable of delivering a formyl equivalent is formamidine acetate.

3. The process as claimed in claim 1 wherein the compound of formula A is the compound 3-amino-2-ethoxycarbonylpyrrole.

4. A process of preparing the compound 3H,5H-pyrrolo[3,2-d]pyrimidin-4-one, comprising the following steps:
   (a) reacting isoxazole with alkoxide ions in the presence of an alcohol;
   (b) quenching the reaction with an acid;
   (c) reacting the resulting reaction mixture with a dialkyl aminomalonate;
   (d) isolating an organic phase of the resulting reaction mixture and reducing it to a residue;
   (e) reacting the residue from the organic phase with a base in a protic or aprotic solvent to produce a compound of formula (A)

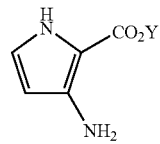

(A)

wherein Y is an unsubstituted or substituted alkyl or arylalkyl group having 1 to 8 carbon atoms; and
   (f) reacting the compound of formula (A) with a reagent capable of delivering a formyl equivalent.

* * * * *

UNITED STATES PATENT AND TRADEMARK OFFICE
CERTIFICATE OF CORRECTION

| | | |
|---|---|---|
| PATENT NO. | : 7,405,297 B2 | |
| APPLICATION NO. | : 11/716100 | |
| DATED | : July 29, 2008 | |
| INVENTOR(S) | : Richard Hubert Furneaux, Peter Charles Tyler and Vern L. Schramm | |

It is certified that error appears in the above-identified patent and that said Letters Patent is hereby corrected as shown below:

In the Specification

Column 1, lines 20-27, should read:

-- STATEMENT OF GOVERNMENT SUPPORT

This invention was made with government support under grant number GM041916 awarded by the National Institutes of Health. The government has certain rights in the invention. --

Signed and Sealed this
Fifteenth Day of September, 2015

Michelle K. Lee
*Director of the United States Patent and Trademark Office*